US012702282B2

(12) United States Patent
Duan

(10) Patent No.: US 12,702,282 B2
(45) Date of Patent: Aug. 11, 2026

(54) CAPSULE ENDOSCOPE

(71) Applicants: Ankon Medical Technologies (Shanghai) Co., LTD, Shanghai (CN); ANX IP HOLDING PTE. LTD., Singapore (SG)

(72) Inventor: Xiaodong Duan, Plano, TX (US)

(73) Assignees: Ankon Medical Technologies (Shanghai) Co., LTD, Shanghai (CN); ANX IP HOLDING PTE. LTD., Singapore (SG)

( * ) Notice: Subject to any disclaimer, the term of this patent is extended or adjusted under 35 U.S.C. 154(b) by 130 days.

(21) Appl. No.: 18/725,812

(22) PCT Filed: Dec. 29, 2022

(86) PCT No.: PCT/CN2022/143639

§ 371 (c)(1),
(2) Date: Jul. 1, 2024

(87) PCT Pub. No.: WO2023/125868

PCT Pub. Date: Jul. 6, 2023

(65) Prior Publication Data

US 2025/0098948 A1 Mar. 27, 2025

(30) Foreign Application Priority Data

Dec. 31, 2021 (CN) ........................ 202111673361.9

(51) Int. Cl.
*A61B 1/00* (2006.01)
*A61B 1/04* (2006.01)

(52) U.S. Cl.
CPC .......... *A61B 1/041* (2013.01); *A61B 1/00016* (2013.01); *A61B 1/00034* (2013.01)

(58) Field of Classification Search
CPC .. A61B 1/041; A61B 1/00016; A61B 1/00034
See application file for complete search history.

(56) References Cited

U.S. PATENT DOCUMENTS

2021/0259531 A1 8/2021 Ming et al.

FOREIGN PATENT DOCUMENTS

| | | | | |
|---|---|---|---|---|
| CN | 101683257 A | | 3/2010 | |
| CN | 104720806 A | | 6/2015 | |
| CN | 107822584 A | | 3/2018 | |
| CN | 109091097 A | * | 12/2018 | ............. A61B 1/041 |
| WO | 2021203687 A1 | | 10/2021 | |

* cited by examiner

*Primary Examiner* — Timothy J Neal
(74) *Attorney, Agent, or Firm* — Treasure IP Group, LLC

(57) ABSTRACT

The present invention provides a capsule endoscope, comprising: an enclosure, including an enclosure main body portion and a first end portion, a second end portion; an image acquisition component, disposed within the first end portion; a circuit processing component, disposed within the enclosure main body portion; and an information sending component, the information sending component including an antenna, the antenna including an antenna arm fixed to the inner wall of the enclosure main body portion, or the inner wall of the enclosure main body portion and the inner wall of the second end portion, the antenna arm connected to the image acquisition component and/or the circuit processing component. The capsule endoscope has excellent internal heat management performance.

9 Claims, 5 Drawing Sheets

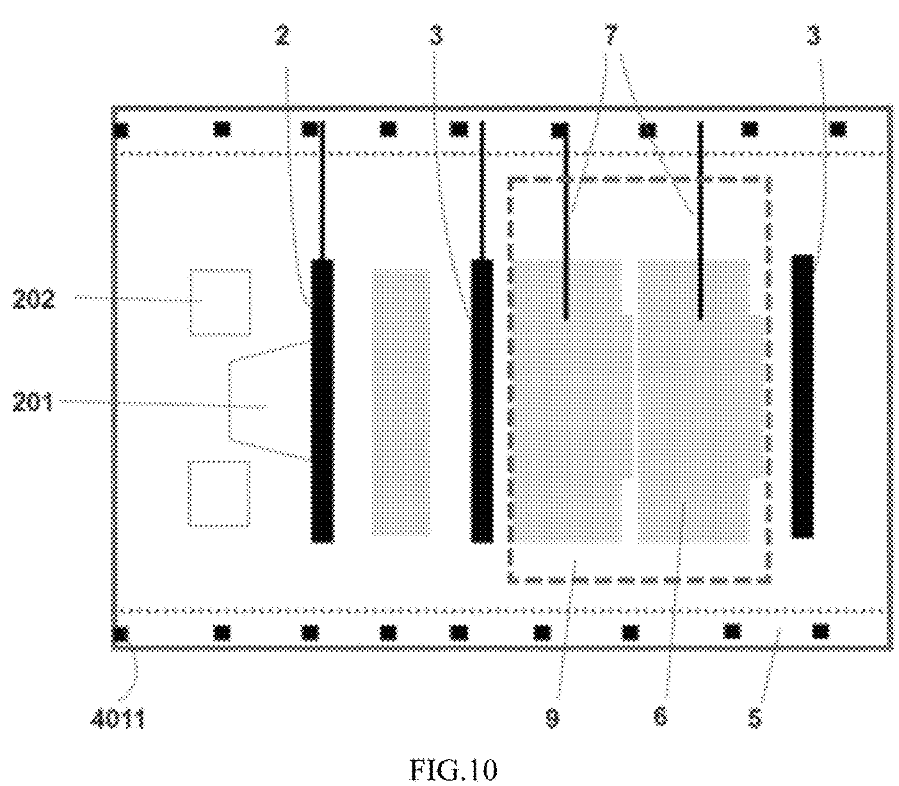
FIG.10
3
4014
4011
1011
FIG.11
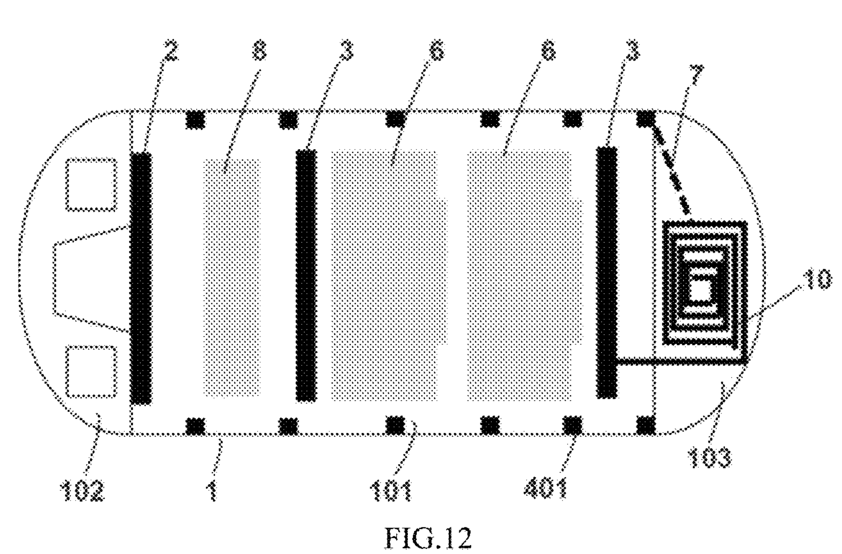
FIG.12

CAPSULE ENDOSCOPE

CROSS-REFERENCE OF RELATED APPLICATIONS

The application is a National Phase Application of PCT International Application No. PCT/CN2022/143639, International Filing Date Dec. 29, 2022, published Jul. 6, 2023 as International Publication Number WO2023/125868A1, which claims priority from Chinese Patent Application No. 202111673361.9, filed Dec. 31, 2021, all of which are incorporated herein by reference in their entirety.

FIELD OF INVENTION

The present invention relates to a capsule endoscope.

BACKGROUND

Capsule endoscope, depending on its high reliability and safety, has become an effective device for diagnosis of gastrointestinal diseases and has obtained high recognition in international medical device field. A capsule endoscope includes a complementary metal oxide semiconductor (abbreviated as CMOS) image sensor, an optical system, a battery, a transmission circuit and an antenna. Images of the gastrointestinal tract of a human subject are formed on the surface of the CMOS image sensor through the optical system. The CMOS image sensor converts light signals into electrical signals, which are then modulated and amplified by the transmission circuit and transmitted through the antenna. These signals are received by an external receiving device and subsequently displayed on a display device. Based on the displayed images, a physician can make a diagnosis of gastrointestinal diseases for the subject in a state of painless and non-invasive gastrointestinal peristalsis.

At this stage, the products on sale, such as PillCam series capsule endoscopes by Given Imaging, EndoCapsule10 series capsule endoscopes by Olympus, and MiroCam series capsule endoscopes by IntroMedic, are mainly used in intestinal examinations where controlled movement is not required, due to their inability to move controllably in the stomach. However, NaviCam series capsule endoscopes by ANKON can be controlled to perform medical examinations in the stomach under the effect of an external magnetic field.

Heat management inside the capsule endoscope has a significant impact on the examination time, imaging quality, and control precision of the capsule endoscope. Due to the limited size of the capsule endoscope, its internal heat management method still needs improvement.

SUMMARY OF THE INVENTION

In order to technically solve above problems of the prior art, the present invention provides a capsule endoscope.

The technical solution of this invention is:

a capsule endoscope, comprising:

an enclosure, comprising an enclosure main body portion (101), a first end portion (102), and a second end portion (103);

an image acquisition component (2) disposed in the first end portion (102);

a circuit processing component (3) disposed in the enclosure main body portion (101); and an information sending component, the information sending component comprising an antenna (401), the antenna (401) comprising an antenna arm (4011) fixed on an inner wall of the enclosure main body portion (101) or on the inner wall of the enclosure main body portion (101) and an inner wall of the second end portion (103), where the antenna arm (4011) is connected to the image acquisition component (2) and/or the circuit processing component (3).

Optionally, the antenna arm (4011) is attached to the inner wall surface of the enclosure main body portion (101), or to the inner wall of the enclosure main body portion (101) and the inner wall surface of the second end portion (103), forming a protruding structure.

Optionally, the surface of the antenna arm (4011) is coated with an electrically insulating and thermally conductive material (5), and/or the inner wall surface of the enclosure main body portion (101), or the inner wall of the enclosure main body portion (101) and the inner wall surface of the second end portion (103), not covered by the antenna arm (4011), are coated with the electrically insulating and thermally conductive material (5).

Optionally, the surface of the antenna arm (4011) is coated with an electrically insulating and thermally conductive material (5), and the inner wall surface of the enclosure main body portion (101), or the inner wall of the enclosure main body portion (101) and the inner wall surface of the second end portion (103), not covered by the antenna arm (4011), are coated with an electrically insulating and thermally conductive material (5). After being coated with the electrically insulating and thermally conductive material (5), the inner surface of the enclosure main body portion (101), or the inner surfaces of the enclosure main body portion (101) and the inner surfaces of the second end portion (103) form a smooth structure with a uniform height and no protrusions.

Optionally, the antenna arm (4011) is connected to the image acquisition component (2) and/or the circuit processing component (3) through a thermally conductive plate (7).

Optionally, the image acquisition component (2) comprises a camera (201) and an illumination device (202), and the antenna arm (4011) is connected to the camera (201) and/or the illumination device (202) through a thermally conductive plate (7).

Optionally, the capsule endoscope further comprises a battery, and the antenna arm (4011) is connected to the battery through a thermally conductive plate (7).

Optionally, the thermally conductive plate (7) connected to the antenna arm (4011) is arranged on the surface of the electrically insulating and thermally conductive material (5).

Optionally, the shape of the antenna (401) is formed by a combination of one or more of a dual-arm helical antenna, a helical antenna, an inverted L antenna, a T-shaped antenna, an umbrella-shaped antenna, a cage antenna, an angular antenna, a V-shaped antenna, a diamond-shaped antenna, a fishbone antenna, a disc-cone antenna, and a biconical antenna.

Optionally, the capsule endoscope further comprises a wireless charging component, the wireless charging component being arranged in the second end portion and electrically connected to the circuit processing component. The thermally conductive plate connects the antenna arm and the wireless charging component.

The advantage of the present invention is providing an effective thermal management and enhancing the battery life of the capsule endoscope without increasing its volume.

BRIEF DESCRIPTION OF THE DRAWINGS

The accompanying drawings, which are included to provide a further understanding of the present invention and are incorporated in and constitute a part of the description, illustrate the embodiment(s) of the present invention and together with the description serve to explain the principle of the invention, but do not constitute a limitation of the present invention. In the drawings:

FIG. 10 is a schematic diagram showing the structural relationship between the antenna and a heat storage material in the capsule endoscope.

FIG. 11 is a schematic diagram showing the connection structure between the enclosure and a circuit processing component in the capsule endoscope.

FIG. 12 is a schematic diagram showing an arrangement of a wireless charging component in the capsule endoscope.

Figure 1:
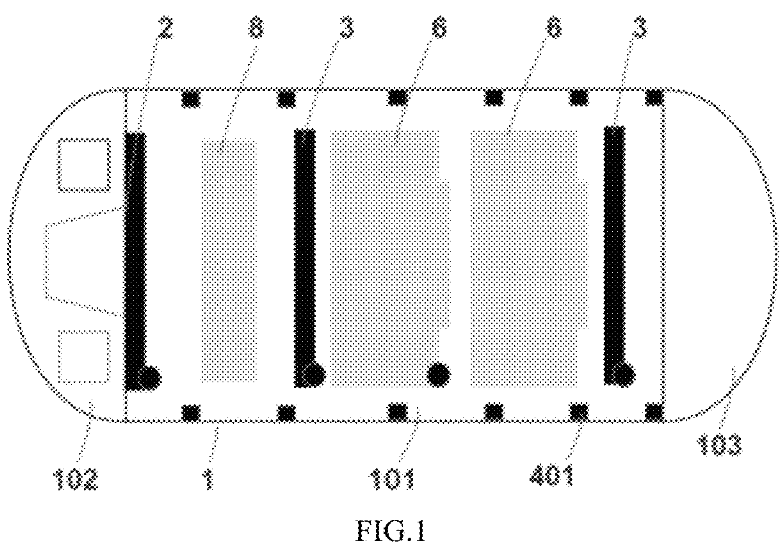
FIG. 1 is a structural schematic diagram of a capsule endoscope according to an embodiment of the present invention.

Elements in the drawings are: 1 enclosure;
101 enclosure main body portion;
1011 housing of enclosure main body portion;
102 first end portion;
103 second end portion;
2 image acquisition component;
201 camera;
202 illumination device;
3 circuit processing component;
401 antenna;
4011 antenna arm;
4012 bottom antenna;
4013 feed port;
4014 connector;
5 electrically insulating and thermally conductive material;
6 battery;
7 thermally conductive plate;
8 permanent magnet;
9 heat storage material;
10 wireless charging component;
1401 thermal insulation material layer.

DETAILED DESCRIPTION

To more clearly understand the objects, features, and advantages of the present invention, a detailed description is provided below in conjunction with the accompanying drawings and specific embodiments. It should be noted that, where there is no conflict, the embodiments and features described in the present invention can be combined with each other.

Many specific details are set forth in the following description to provide a thorough understanding of the present invention. However, the present invention can be practiced in other ways than those specifically described herein. Therefore, the scope of the present invention is not limited by the specific embodiments disclosed below.

As shown in FIGS. 1-13, the present invention provides a capsule endoscope. The capsule endoscope comprises an enclosure (1), the enclosure comprises an enclosure main body portion (101), a first end portion (102) and a second end portion (103). The enclosure main body portion (101) of the capsule endoscope is cylindrical, the first end portion (102) is semi-ellipsoidal, and the second end portion (103) is semi-ellipsoidal. The combination of the enclosure main body portion, the first end portion and the second end portion forms a capsule-shaped endoscope, which is convenient for swallowing and examination. The capsule endoscope further comprises an image acquisition component (2) disposed within the first end portion (102), a circuit processing component (3) disposed within the enclosure main body portion (101), and an information sending component. The information sending component comprises an antenna (401), the antenna (401) is fixed on the inner wall of the enclosure main body portion (101), or on the inner wall of the enclosure main body portion (101) and the inner wall of the second end portion (103). The antenna (401) is connected to the image acquisition component (2) and/or the circuit processing component (3).

The circuit processing component (3) is composed of one or more of a processor, an image accelerator, a power management integrated circuit (abbreviated as PMIC), an accelerometer, a six-axis sensor, a light sensor, and an infrared sensor.

The capsule endoscope further comprises a battery (6) that supplies power to the various components of the capsule endoscope and is controlled by the PMIC. The antenna (401) is attached to the inner wall of the enclosure of the capsule endoscope. Specifically, the antenna (401) may be fixed only to the inner wall of the enclosure main body portion (101), and may also be fixed simultaneously to the inner wall of the main body portion and the inner wall of the second end portion (103) opposite the image acquisition component (2). The antenna (401) is a protruding structure.

The antenna (401) has a heat conduction function. According to the basic formula of heat conduction "$Q=K\times A\times\Delta T/\Delta L$", the amount of heat transfer Q is directly proportional to the thermal conductivity coefficient K and the heat transfer area A, and inversely proportional to the distance $\Delta L$. The higher the thermal conductivity coefficient and the larger the heat transfer area, the shorter the transfer distance, the higher the energy of thermal conduction, and the easier it is to dissipate heat. When the antenna is simultaneously fixed to the inner wall of the enclosure main body portion (101) and the inner wall of the second end portion (103) opposite the image acquisition component (2), compared with being fixed only to the inner wall of the enclosure main body portion (101), the antenna (401) covers more of the inner wall of the second end portion (103). The area of the antenna (401) is larger, resulting in a larger heat transfer area and better heat conduction effect.

Figure 2:
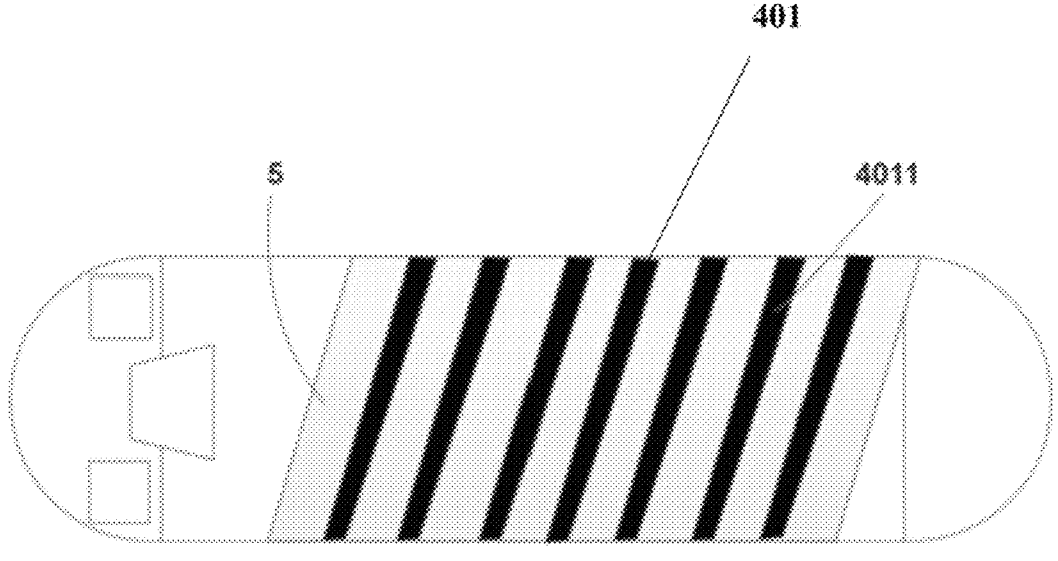
FIG. 2 is a structural schematic diagram of an antenna of the capsule endoscope.

FIG. 2 is a structural schematic diagram of an antenna of the capsule endoscope. As shown in FIG. 2, the antenna comprises an antenna arm (4011) fixed to the inner wall of the enclosure main body portion (101), or to the inner wall of the enclosure main body portion (101) and the inner wall of the second end portion (103).

Figure 3:
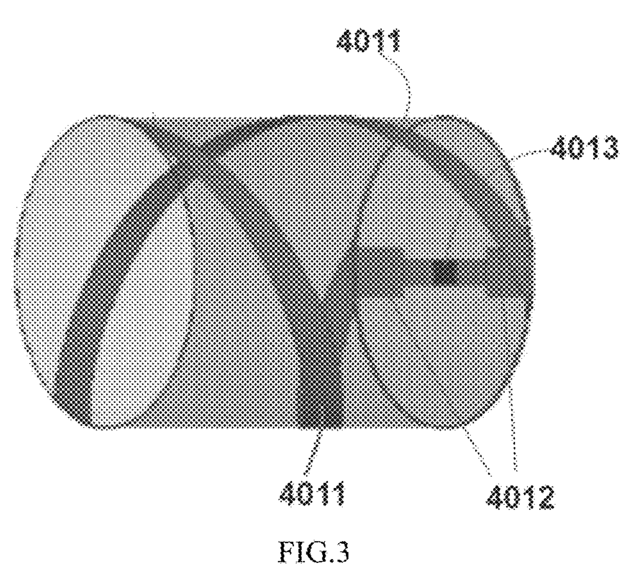
FIG. 3 is a schematic diagram showing an antenna arm of the antenna wrapped around an inner wall of an enclosure of the capsule endoscope in FIG. 2.

The main structure of the antenna (401) is the antenna arm (4011). Specifically, as shown in FIG. 3, the antenna is divided into the antenna arm (4011) and a bottom antenna (4012). The bottom antenna (4012) is placed in the second end portion (103) opposite the image acquisition component (2), and the antenna arm (4011) is connected to the bottom antenna (4012). The bottom antenna (4012) has a feed port (4013) for connecting to the circuit processing component (3).

The antenna (401) can be made into a helical shape and installed inside the enclosure of the capsule endoscope by rotation. The helical antenna has a tendency to expand outward, which is constrained by the enclosure of the capsule endoscope, forming a stable fixed structure between the antenna (401) and the enclosure of the capsule endoscope.

The shape of the antenna arm (4011) can be formed by a combination of one or more of a dual-arm helical antenna, a helical antenna, an inverted L antenna, a T-shaped antenna, an umbrella-shaped antenna, a cage antenna, an angular antenna, a V-shaped antenna, a diamond-shaped antenna, a fishbone antenna, a disc-cone antenna, and a biconical antenna.

In the preferred embodiment, as shown in FIG. 3, the antenna arm is a dual-arm helical antenna. The helical setting of the antenna arm is adapted to the inner wall of the enclosure of the capsule endoscope, making it relatively flat and attached to the inner wall. A copper foil as an antenna, with the wide side in contact with the inner wall, capable of increasing the contact area with the inner wall while being attached to it.

The antenna arm (4011) is made of copper foil with a width of 1 mm-10 mm. Copper has a high thermal conductivity coefficient, which allows it to quickly conduct heat to the entire antenna arm (4011). The thickness of the antenna arm (4011) is 0.1 mm-1 mm.

FIG. 3 shows a situation where the antenna arm (4011) is arranged around the inner wall of the enclosure of the capsule endoscope. FIG. 2 shows a side view of the antenna arm (4011) regularly and helically arranged around the inner wall of the enclosure of the capsule endoscope. The antenna arm (4011) is an overall continuous structure, but the present invention is not limited to this. As can be seen from FIG. 2, in the case where the antenna arm (4011) is regularly wound around the inner wall of the enclosure of the capsule endoscope, the antenna arm (4011) can be regarded as including multiple antenna arm (4011) portions, with intervals between the antenna arm (4011) portions.

The antenna arm (4011) is connected to the image acquisition component (2) and/or the circuit processing component (3). In one embodiment, the antenna arm (4011) is connected to the image acquisition component (2) and/or the circuit processing component (3) via a thermally conductive wire (not shown in the figures). The thermal conductive wire may be a metal wire, etc. The information sending component of the capsule endoscope comprises an antenna (401) composed of the antenna arm (4011) and a radio frequency circuit (not shown in the figures). In working mode, the camera component (201) captures images of the digestive tract and transmits them to the circuit processing component for processing. The image data processed by the circuit processing component (3) is ultimately transmitted to an external image display device via a radio frequency circuit board and the antenna (401) in the information sending component.

The antenna arm (4011) is connected to the image acquisition component (2) and/or the circuit processing component (3) through a thermally conductive wire (not shown in the figures), so that the heat from the image acquisition component (2) and/or the circuit processing component (3) can be quickly conducted to the antenna arm (4011). Since the antenna arm (4011) is made of metal and has good thermal conductivity, it can evenly conduct the heat transferred from the image acquisition component (2) and/or the circuit processing component (3) to the inner wall of the enclosure of the capsule endoscope. The larger the area coverage of the antenna arm (4011), the better the heat conduction effect and the more uniform the heat transfer. Considering the actual working needs of the capsule endoscope, the area coverage of the antenna arm (4011) in the enclosure of the capsule endoscope can be 10%-85%, preferably 20%-45%.

Since the antenna arm (4011) does not cover the entire inner wall of the enclosure of the capsule endoscope, heat can be transferred to the inner wall of the enclosure of the capsule endoscope where the antenna arm (4011) is arranged. However, due to the intervals between the multiple portions of the antenna arm (4011), the heat transferred to the antenna arm (4011) cannot effectively dissipate in the intervals where the antenna arm (4011) is not set, easily causing heat accumulation.

In the embodiment, the antenna arm (4011) is encapsulated with an electrically insulating and thermally conductive material, and the surface of the antenna arm (4011) is coated with the electrically insulating and thermally conductive material (5). Additionally, the inner wall surface of the enclosure main body portion (101), or the inner wall of the enclosure main body portion (101) and the inner wall surface of the second end portion (103), not covered by the antenna arm (4011), are coated with the electrically insulating and thermally conductive material (5).

For clarity, FIG. 2 shows that the inner wall surface of the enclosure main body portion (101), or the inner wall of the enclosure main body portion (101) and the inner wall surface of the second end portion (103), not covered by the antenna arm (4011), are coated with the electrically insulating and thermally conductive material (5). In fact, the surface of the antenna arm (4011) is also covered with the electrically insulating and thermally conductive material (5).

Figure 4:
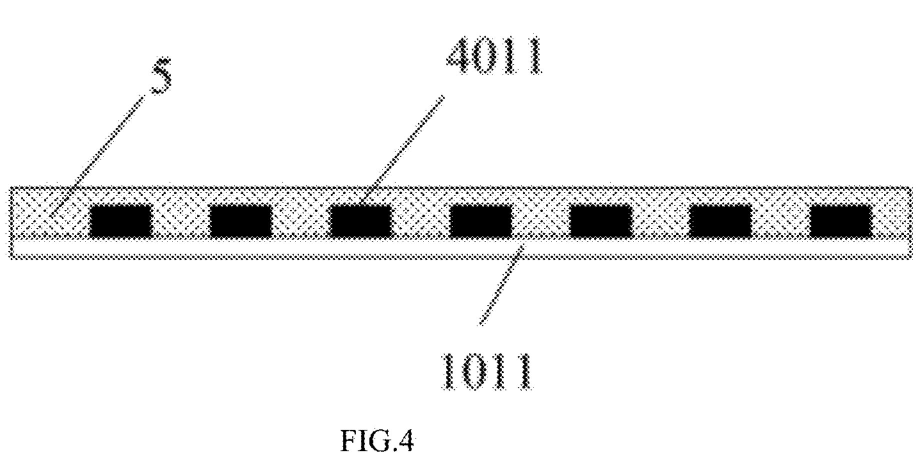
FIG. 4 is a cross-sectional view of an enclosure main body portion of the capsule endoscope.
Figure 5:
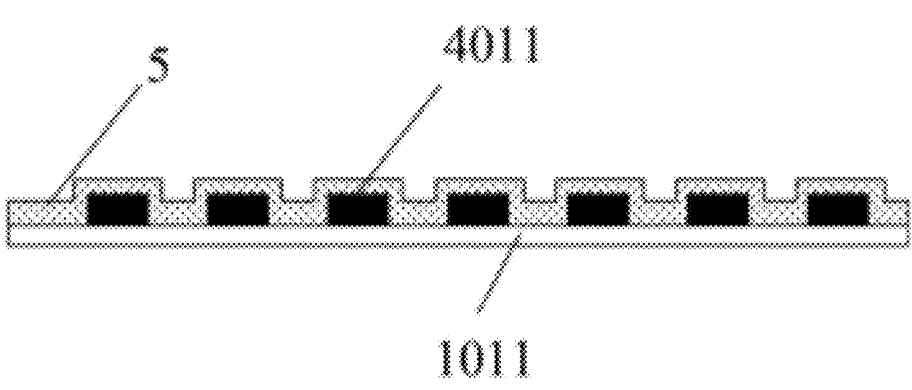
FIG. 5 is a cross-sectional view of another enclosure main body portion of the capsule endoscope in FIG. 4.

FIGS. 4 and 5 show cross-sectional diagrams of the enclosure main body portion (101) of the capsule endoscope. As shown in FIG. 4, the surface of the antenna arm (4011) is coated with the electrically insulating and thermally conductive material (5), the inner wall surface of the enclosure main body portion (101) and the inner wall surface of the second end portion (103) (only the inner wall surface of the main body part 101 is shown in FIG. 3), which are not covered by the antenna arm (4011), are coated with the electrically insulating and thermally conductive material (5). The inner surface of the enclosure main body portion (101), or the inner surface of the enclosure main body portion (101) and the second end portion (103), after being coated with the electrically insulating and thermally conductive material (5), has a smooth structure with a uniform height and no protrusions.

As shown in FIG. 5, after coating with the electrically insulating and thermally conductive material (5), the inner wall surface of the enclosure main body portion (101) may also be an uneven surface, and the present invention is not limited to this. FIGS. 4 and 5 only illustrate the inner wall of the enclosure main body portion (101) as an example. The same applies to the second end portion (103), which is not elaborated here.

The electrically insulating and thermally conductive material (5) is closely attached to the antenna arm (4011), allowing the heat received by the antenna arm (4011) with heat dissipation function to be quickly conducted to the entire enclosure of the capsule endoscope, including the intervals of the antenna arm (4011). The thickness of the electrically insulating and thermally conductive material (5) is 0.01 mm-0.1 mm.

Figure 6:
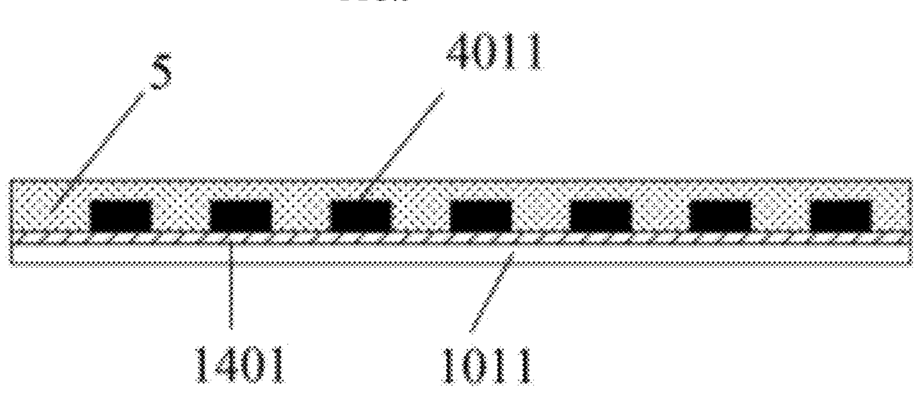
FIG. 6 is a cross-sectional view of an interlayer of the enclosure main body portion of the capsule endoscope.
Figure 7:
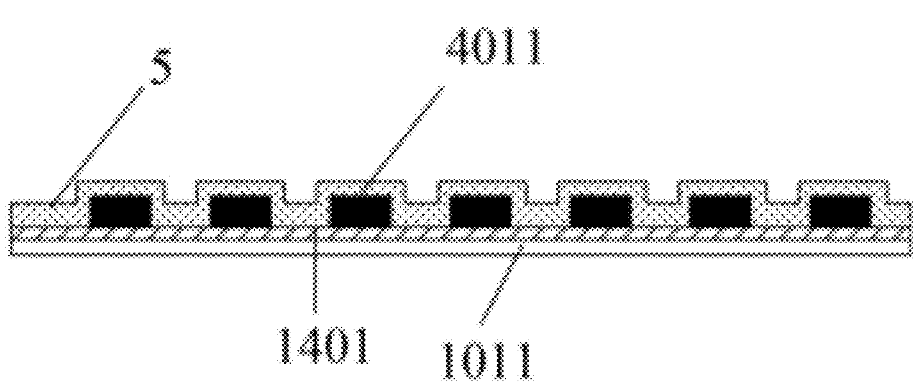
FIG. 7 is a cross-sectional view of another interlayer of the enclosure main body portion of the capsule endoscope in FIG. 6.

In another embodiment, as shown in FIGS. 6 and 7, an thermal insulation material layer (1401) can also be provided between the antenna arm (4011) and the enclosure of the capsule endoscope. This allows the antenna to quickly conduct the heat received from the image acquisition component (2) and/or the circuit processing component to the entire enclosure of the capsule endoscope, avoiding localized excessive heat. At the same time, the thermal insulation material layer (1401) can retain the heat within the capsule endoscope rather than dissipating it outward through the enclosure, thereby accumulating the heat inside the capsule endoscope to extend battery life. The thermal insulation material layer (1401) may comprises insulating materials with poor thermal conductivity, such as nano-insulation film, plastic film technology (abbreviated as PFT) film, polyester film, polyimide film, etc. The present invention is not limited to these.

As previously mentioned, the reason why the heat generated by the image acquisition component and the circuit processing component can be transferred to the antenna arm (4011) is that the image acquisition component and the circuit processing component are connected to the antenna arm (4011) through a thermally conductive wire.

Figure 8:
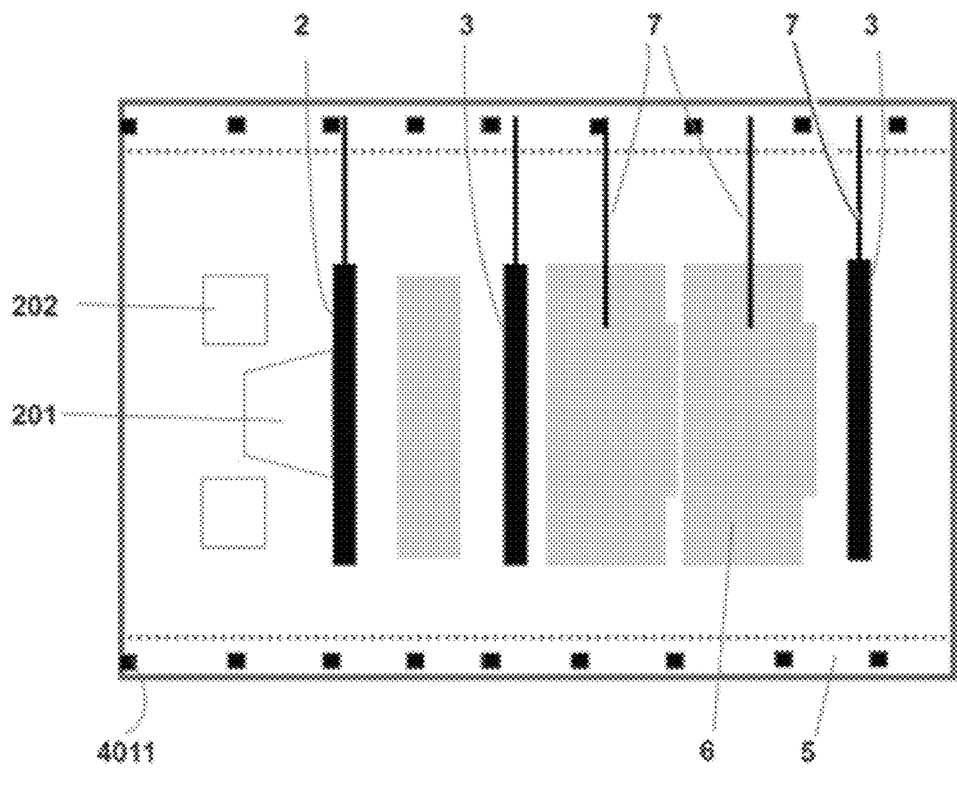
FIG. 8 is a schematic diagram showing a connection structure of a thermally conductive plate in the capsule endoscope.

In one embodiment of the present invention, a capsule endoscope is provided. As shown in FIG. 8, a thermally conductive plate (7) is arranged between the antenna arm (4011) and the image acquisition component (2) and the circuit processing component (3). The antenna arm (4011) is connected to the image acquisition component (2) and the circuit processing component (3) through the thermally conductive plate (7). The thermally conductive plate (7) increases the heat transfer path from the image acquisition component (2) and the circuit processing component (3) to the antenna arm (4011), allowing heat to be transferred to the antenna arm (4011) more efficiently.

Figure 9:
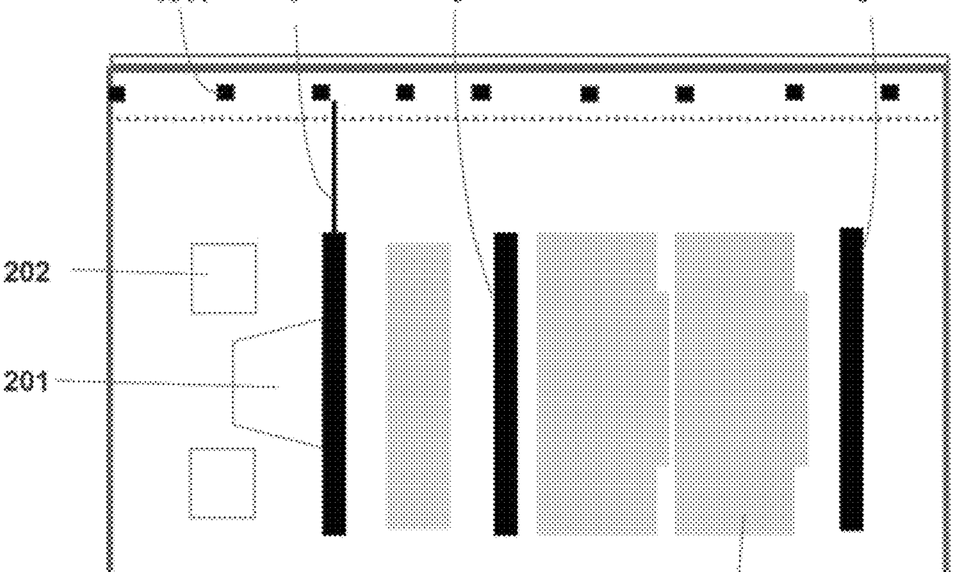
FIG. 9 is a schematic diagram showing another connection structure of the thermally conductive plate in the capsule endoscope in FIG. 8.

The image acquisition component (2) comprises or consists of a camera (201) and an illumination device (202). As shown in FIG. 9, the antenna arm (4011) is connected to the camera (201) and/or the illumination device (202) through the thermally conductive plate (7). The illumination device (202) can be light emitting diodes.

As previously mentioned, accumulating heat inside the capsule endoscope rather than dissipating it through the enclosure can extend battery life. To better supply heat for battery use, in one embodiment of the present invention, as shown in FIG. 10, a thermally conductive plate (7) is arranged between the battery (6) and the antenna arm in the capsule endoscope. The antenna arm (4011) is connected to the battery (6) through the thermally conductive plate (7), which can directly transfer the heat received by the antenna arm (4011) to the battery (6) for use, thereby extending the battery life.

Further, a heat storage material (9) is arranged around the battery (6). As shown in FIG. 10, the heat from the antenna arm (4011) can be conducted into the heat storage material (9) through the thermally conductive plate (7) and stored therein, so that the heat is slowly released during the long-term examination process of the capsule endoscope, maintaining the operation of the battery within an effective working temperature range. The heat of the antenna arm (4011) comes from the image acquisition component (2) and the circuit processing component (3), and is transferred to the antenna arm (4011) through the thermally conductive plate (7).

The material of the thermally conductive plate (7) may comprise an electrically insulating material with good thermal conductivity. In one embodiment, the thermally conductive plate (7) may be connected to the electrically insulating and thermally conductive material (5) arranged on the surface of the antenna arm (4011), and connected to the antenna arm (4011) through the electrically insulating and thermally conductive material (5).

The thermally conductive plate (7) can be made from a material with high thermal conductivity, such as thermally conductive adhesive, thermally conductive insulating sheet, or thermally conductive silicone.

Optionally, the number of thermally conductive plates (7) connected to the battery (6) may be two, three, four, or more. Compared to a single thermally conductive plate (7), multiple thermally conductive plates (7) can transfer heat more quickly, rapidly conveying the heat received by the antenna arm (4011) directly to the battery (6) for use, thereby extending the battery's usage time.

The capsule endoscope has a small volume but a very complex structure. The heat generated during its operation is difficult to dissipate quickly. Conducting the heat to the enclosure of the capsule endoscope through an antenna can enhance heat dissipation and improve thermal management capability. The material of enclosure of the capsule endoscope may typically be: polycarbonate (abbreviated as PC), polymethyl methacrylate (abbreviated as PMMA), optical polyester resin, etc. These materials are all resin, with good plasticity. The antenna arm (4011) can be integrally formed with the housing of the enclosure main body portion (1011) during production, that is, after the production of the antenna arm (4011) is completed, it is injection molded to form the enclosure main body portion of the capsule endoscope. Connectors (4014) are respectively provided on the circuit processing component (3) and the corresponding inner wall of the housing of the enclosure main body portion (1011) of the capsule endoscope, as shown in FIG. 11. During the assembly process, the circuit processing component (3) is pushed into the enclosure so that the two connectors (4014) connect, thereby achieving electrical connection and meeting the radio frequency requirements of the capsule endoscope. The connectors (4014) preferably use contacts that are less difficult to process, ensuring effective electrical connection.

In order to extend the battery life of the capsule endoscope, a wireless charging component is installed in the capsule endoscope, and the wireless charging component comprises a receiving coil and a rectifier circuit. In a gastrointestinal examination, an external magnetic control device will be used in conjunction with the capsule endoscope for a controlled examination. During this stage, wireless charging can be performed. After completing the stomach examination, the capsule endoscope enters the intestine through natural peristalsis for intestinal examination, and is finally excreted from the body. Capsule endoscope takes a longer time for intestinal examination, far exceeding the time it stays in the stomach. However, wireless charging can only be performed during the stomach examination and cannot be done in the intestine. Therefore, there is still the issue of insufficient battery life for the capsule endoscope during intestinal examination. Additionally, the wireless charging component generates heat while operating. If this heat is not managed, it will accumulate and cause the local temperature of the enclosure of the capsule endoscope to become too high, making the patient feel uncomfortable.

In another embodiment, as shown in FIG. 12, to address the issue of localized overheating of the enclosure of the capsule endoscope, the wireless charging component (10) is disposed in the second end portion (103). The wireless charging component (10) is electrically connected to the circuit processing component (3), and the wireless charging component (10) transfers the obtained electrical energy to the battery (6) for storage through the circuit processing component (3). The thermally conductive plate (7) is used to connect the antenna arm (4011) and the wireless charging component (10). The heat generated by the wireless charging component during operation is quickly transferred to the antenna arm (4011) through the thermally conductive plate (7), achieving heat conduction and preventing heat accumulation.

Figure 13:
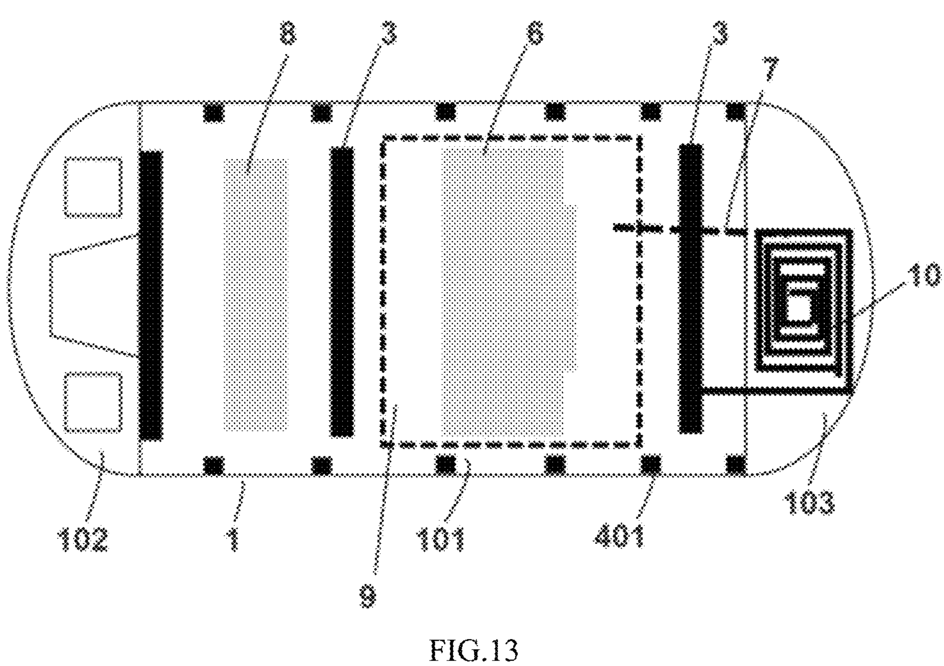
FIG. 13 is a schematic diagram showing another arrangement of the wireless charging component in the capsule endoscope.

In another embodiment, to address the issue of insufficient battery life, as shown in FIG. 13, the wireless charging component (10) is disposed in the second end portion (103). The wireless charging component (10) is electrically connected to the circuit processing component (3), and the wireless charging component (10) transfers the obtained electrical energy to the battery (6) for storage through the circuit processing component (3). The battery (6) is surrounded by a heat storage material (9), and a thermally conductive plate (7) is used to connect the wireless charging component (10) and the heat storage material (9). The heat generated by the wireless charging component (10) during operation enters the heat storage material through the thermally conductive plate. After the capsule endoscope enters the intestine, it will autonomously take images for several hours. The heat storage material releases heat slowly, which activates the battery (6), maintains the battery at a higher operating temperature, extends working time of the battery, and avoids the problem of heat accumulation causing discomfort to the patient.

The battery (6) is one or two silver oxide batteries, or a silver oxide battery and a secondary battery used for wireless charging. Preferably, a silver oxide battery and a lithium battery are used. During examination, the lithium battery is supplied with power first, usually for stomach examination. After completing the stomach examination, the external magnetic control device wirelessly charges the capsule endoscope. Once the lithium battery is fully charged, the intestinal examination is conducted. Compared to using two silver oxide batteries, the combination of one silver oxide battery and one lithium battery in a wireless charging setup can provide longer battery life.

As shown in FIG. 1, the capsule endoscope comprises a permanent magnet (8), and the permanent magnet (8) is disposed in the enclosure. The permanent magnet (8) makes the capsule endoscope magnetic, allowing it to be coordinated with an external magnetic control device to adjust its position, posture, and direction. Optionally, a second permanent magnet (not shown) is provided inside the second end portion (103), which can be cylindrical, spherical, or preferably ellipsoidal and concentric with the second end portion. The ellipsoidal permanent magnet can be in close contact with the inner wall of the second end portion. The permanent magnet (8) is close to the first end portion, and the second permanent magnet is close to the second end portion. The two permanent magnets can balance the weight of the capsule endoscope, and in conjunction with an external magnetic control device, generate two magnetic torques, allowing for precise adjustment of the capsule endoscope's position, posture, and direction.

According to the embodiments of the present invention, the heat generated by the image acquisition component and/or the circuit processing component is rapidly conducted to the antenna arm, and is evenly distributed through the antenna arm to reduce local heat accumulation, or a heat storage material is used to store excess heat near the battery and release it slowly, optimizing discharge capability of the battery. This achieves effective thermal management and avoids discomfort caused by excessive temperature for the patient.

The above descriptions are only preferred embodiments of the present invention, and are not intended to limit the present invention. For those skilled in the art, the present invention may have various modifications and changes. Any modifications, equivalent replacements, improvements, etc. made within the spirit and principles of the present invention shall be included within the protection scope of the present invention.

The invention claimed is:

1. A capsule endoscope, comprising:

an enclosure, comprising an enclosure main body portion, a first end portion and a second end portion;

an image acquisition component, comprising a camera and an illumination device, disposed in the first end portion;

a circuit processing component, comprising a processor, an image accelerator, a power management integrated circuit (PMIC), an accelerometer, a six-axis sensor, a light sensor, and an infrared sensor, disposed in the enclosure main body portion; and an information sending component, wherein the information sending component comprising an antenna, the antenna comprising an antenna arm fixed on an inner wall of the enclosure main body portion or on the inner wall of the enclosure main body portion and an inner wall of the second end portion, and the antenna arm is connected to the image acquisition component and/or the circuit processing component, wherein the surface of the antenna arm is coated with an electrically insulating and thermally conductive material.

2. The capsule endoscope of claim 1, wherein the antenna arm is attached to the inner wall surface of the enclosure main body portion, or to the inner wall of the enclosure main body portion and the inner wall surface of the second end portion, forming a protruding structure.

3. The capsule endoscope of claim 1, wherein the inner wall surface of the enclosure main body portion, or the inner wall of the enclosure main body portion and the inner wall surface of the second end portion, not covered by the antenna arm are coated with the electrically insulating and thermally conductive material.

4. The capsule endoscope of claim 3, wherein after being coated with the electrically insulating and thermally conductive material, the inner surface of the enclosure main body portion, or the inner surfaces of the enclosure main body portion and the inner wall surface of the second end portion form a smooth structure with a uniform height and no protrusions.

5. The capsule endoscope of claim 4, wherein the thermally conductive plate connected to the antenna arm is arranged on the surface of the electrically insulating and thermally conductive material.

6. The capsule endoscope of claim 1, wherein the antenna arm is connected to the image acquisition component and/or the circuit processing component through a thermally conductive plate.

7. The capsule endoscope of claim 1, wherein the capsule endoscope further comprises a battery, and the antenna arm is connected to the battery through a thermally conductive plate.

8. The capsule endoscope of claim 1, wherein a thermal insulation material layer is provided between the antenna arm and the enclosure.

9. The capsule endoscope of claim 1, wherein the capsule endoscope further comprises a wireless charging component and a battery, the wireless charging component is arranged in the second end portion and electrically connected to the circuit processing component, and charges the battery through the circuit processing component; and the capsule endoscope further comprises a thermally conductive plate connecting the antenna arm and the wireless charging component.

* * * * *